(12) United States Patent
Gittos

(10) Patent No.: US 7,189,742 B2
(45) Date of Patent: Mar. 13, 2007

(54) PIPERIDIN-2,6-DIONE BISULPHATE SALTS AND THEIR USE FOR THE TREATMENT OF STRESS RELATED AFFECTIVE DISORDERS

(75) Inventor: Maurice Ward Gittos, Plobsheim (FR)

(73) Assignee: Prestwick Pharmaceuticals, Inc., Washington, DC (US)

( * ) Notice: Subject to any disclaimer, the term of this patent is extended or adjusted under 35 U.S.C. 154(b) by 525 days.

(21) Appl. No.: 10/486,925

(22) PCT Filed: Aug. 22, 2002

(86) PCT No.: PCT/GB02/03869

§ 371 (c)(1),
(2), (4) Date: Feb. 25, 2004

(87) PCT Pub. No.: WO03/020275

PCT Pub. Date: Mar. 13, 2003

(65) Prior Publication Data

US 2004/0249159 A1 Dec. 9, 2004

(30) Foreign Application Priority Data

Aug. 28, 2001 (GB) ................................. 0120821.4

(51) Int. Cl.
*C07D 211/40* (2006.01)
*A61K 31/45* (2006.01)

(52) U.S. Cl. ...................................... 514/328; 546/220

(58) Field of Classification Search ................ 514/328; 546/220

See application file for complete search history.

(56) References Cited

U.S. PATENT DOCUMENTS 4,835,151 A * 5/1989 Gittos ........................ 514/219

OTHER PUBLICATIONS

Hasegawa et al., The Tryptophan Hydroxylase Activation Inhibitor, AGN-2979, Decreases Regional 5-HT Synthesis in the Rat Brain Measured with α-[14C]Methyl-L-Tryptophan: An Autoradiographic Study, Brain Research Bulletin, 67:248-255 (2005).*

* cited by examiner

*Primary Examiner*—Celia Chang
*Assistant Examiner*—R. James Balls
(74) *Attorney, Agent, or Firm*—Bacon & Thomas, PLLC

(57) ABSTRACT

Novel bisulphate salts of certain 3-phenyl-3-dimethylaminoalkyl-4,4-dimethylpiperidin-2,6-diones and pharmacologically acceptable solvates thereof are devoid of the weight loss and hepatocyte changes in the rat which limited to marginally effective levels the permitted clinical doses of the corresponding hydrochlorides in the treatment or prophylaxis of stress-related affective disorders such as anxiety, depression, migraine and sleep apnea. The preferred bisulphate salts are 3(3,5-dimethoxyphenyl)-3-(3-dimethylaminopropyl)-4,4-dimethylpiperidine-2,6-dione bisulphate and, especially, 3(3-methoxyphenyl)-3-(3-dimethylaminopropyl)-4,4-dimethylpiperidine-2,6-dione bisulphate.

21 Claims, 2 Drawing Sheets

PIPERIDIN-2,6-DIONE BISULPHATE SALTS AND THEIR USE FOR THE TREATMENT OF STRESS RELATED AFFECTIVE DISORDERS

CROSS-REFERENCE TO RELATED APPLICATIONS

This is filing under 35 U.S.C. 371 of PCT/GB02/03869, filed 22 Aug. 2002, which claims priority from United Kingdom Application No. 0120821.4 filed 28 Aug. 2001.

The present invention relates to hydrogen sulphate (i.e. bisulphate) salts of certain 3-phenyl-3-dimethylaminoalkyl-4,4-dimethylpiperidin-2,6-diones and their use in the treatment of stress-related affective disorders. The term "stress-induced affective disorder" is used herein to include any disorder associated with elevated levels of 5-HT (5-hydroxytryptamine; serotonin) resultant from newly synthesised 5-HT.

3-Phenyl-3-dimethylaminoalkyl-4,4-dimethylpiperidin-2,6-diones of the following Formula I and their acid addition salts have been known since 1974 (see BE-A-808,958; corresponding to GB-A-1,455,687 & U.S. Pat. No. 3,963,729):

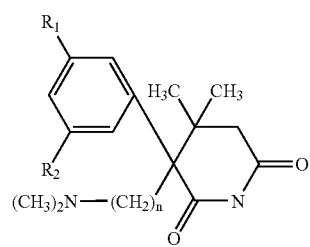

(I)

wherein:
$R_1$ represents methoxy, ethoxy or hydroxy;
$R_2$ represents methoxy, ethoxy, hydroxy or hydrogen; and
n represents 2 or 3.

They have been reported to have a range of pharmacological activities (see U.S. Pat. Nos. 3,963,729; 4,461,771; 4,738,973; 4,835,151; 4,835,151; 4,918,084; 4,994,475; 5,177,086; GB-A-2,196,251 & GB-A-2,206,491) but were primary of interest for the treatment of stress-related affective disorders, especially anxiety and depression. They are the only compounds presently known to block selectively the activation of tryptophan hydroxylase induced by depolarisation, metabolic inhibitors, methyl xanthine, or stress. The compound of choice for clinical investigation was 3(3-methoxyphenyl)-3-(3-dimethylaminopropyl)-4,4-dimethylpiperidine-2,6-dione, which has been variously identified as AGN 2979 (which designation will be used in this application); BTG 1501; MDL 72415 and SC 48274. A large number of acid addition salts of AGN 2979 have been proposed but the hydrochloride has been the salt of choice because hydrochloride acid addition salts are the most commonly used acid addition salts and can be readily and inexpensively prepared and there was no reason to believe that any other salts would have any advantage over the hydrochloride. There has been no previous proposal or suggestion to use a bisulphate salt of AGN 2979, or of any other base of Formula 1 or other 3-phenyl substituted-3-dialkylaminoalkyl-4,4-dialkylpiperidin-2,6-dione, for any purpose.

A number of papers relating to clinical trials of the hydrochloride salt of AGN 2979 have been conducted and the results published. These showed the salt to be effective in the treatment of anxiety and depression at about 4 mg/kg/day (200–400 mg/day for human patients). However, a 1-year sub-acute toxicity study of the hydrochloride (200 mg/kg/day p o. (i.e. by mouth)) in rats showed that the animals suffered an immediate and continuing weight loss (40% over the 1-year period) and, as revealed by post-mortem examination, hepatocyte changes which had not been detected by routine transaminase determinations during the year. As a result, the USA Food and Drugs Administration ("F.D.A") precluded the use of the dose levels previously used in the clinical trials. A subsequent clinical study by Cutler et al using an F.D.A. allowed dose of 1 mg b.i.d. (i.e. twice daily) (about 30 µg/kg/day) showed that the hydrochloride salt of AGN 2979 possessed only marginally effective anxiolytic properties at FDA permitted dose levels.

It has now surprisingly been found that the aforementioned problems of weight loss and hepatocyte changes can be overcome by the use of the bisulphate salt instead of the hydrochloride, or other previously disclosed salt, of compounds of Formula 1. These bisulphate salts do not cause weight loss and the indications are that they will not cause hepatocyte changes over prolonged periods of treatment.

Thus, according to a first aspect of the present invention, there is provided the bisulphate salts of 3-phenyl-3-dimethylaminoalkyl-4,4-dimethylpiperidin-2,6-diones of Formula I:

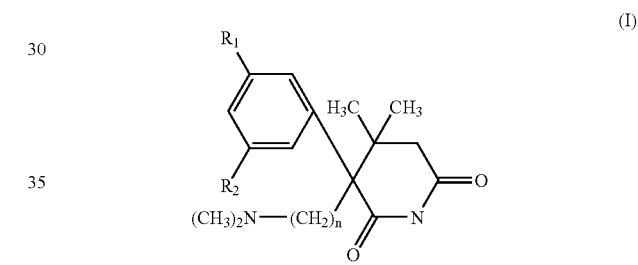

(I)

wherein:
$R_1$ represents methoxy, ethoxy or hydroxy;
$R_2$ represents methoxy, ethoxy, hydroxy or hydrogen; and
n represents 2 or 3,
and pharmacologically acceptable solvates thereof.

The compounds of Formula 1 exist in optical isomers and accordingly the bisulphate salts can be used in racemate form or as individual (+) or (−) isomers. Presently the (−) isomer is preferred. The salts can exist in solvated, especially, hydrated, form and can hydrate on storage in a non-airtight environment. In the case of AGN 2979, the bisulphate hydrates by water vapour sorption to form the sesquihydrate.

In a second aspect, the present invention provides methods for the treatment or prophylaxis of stress-related affective disorders which comprise administering to a human or animal patient an effective amount of a bisulphate salt of a compound of Formula I or a pharmacologically acceptable solvate thereof.

In a third aspect, the present invention provides pharmaceutical compositions comprising the bisulphate salt of a compound of Formula 1 or a pharmacologically acceptable solvate thereof and a pharmacologically acceptable diluent or carrier.

In a fourth aspect, the present invention provides the bisulphate salts of compounds of Formula I and pharmacologically acceptable solvates thereof for use in treatments of the human or animal body by therapy or diagnosis practised on the human or animal body.

In a fifth aspect, the present invention provides the use of bisulphate salts of compounds of Formula I and pharmacologically acceptable solvates thereof in the manufacture of medicaments for the treatment or prophylaxis of stress-related affective disorders.

Examples of bisulphate salts of compounds of Formula I include the following:

3-(3'-methoxyphenyl)-3-(2"-N,N-dimethylaminoethyl)-4,4-dimethylpiperidin-2,6-dione bisulphate;

3-(3'-methoxyphenyl)-3-(3"-N,N-dimethylaminopropyl)-4,4-dimethylpiperidin-2,6-dione bisulphate;

3-(3'-hydroxyphenyl)-3-(2"-N,N-dimethylaminoethyl)-4,4-dimethylpiperidin-2,6-dione bisulphate;

3-(3'-hydroxyphenyl)-3-(3"-N,N-dimethylaminopropyl)-4,4-dimethylpiperidin-2,6-dione bisulphate;

3-(3'-ethoxyphenyl)-3-(3"-N,N-dimethylaminopropyl)-4,4-dimethylpiperidin-2,6-dione bisulphate;

3-(3',5'-dimethoxyphenyl)-3-(3"-N,N-dimethylaminopropyl)-4,4-dimethylpiperidin-2,6-dione bisulphate;

3-(3',5'-dihydroxy)-3-(3"-N,N-dimethylaminopropyl)-4,4-dimethylpiperidin-2,6-dione bisulphate; and 3-(3',5'-diethoxy)-3-(3"-N,N-dimethylaminopropyl)-4,4-dimethyl-piperidin-2,6-dione bisulphate.

The preferred bisulphate salts are those of compounds of Formula 1 in which $R_1$ represents methoxy and $R_2$ represents methoxy or hydrogen. The most preferred salts are 3(3,5-dimethoxyphenyl)-3-(3-dimethylaminopropyl)-4,4-dimethylpiperidine-2,6-dione bisulphate and, especially, 3(3-methoxyphenyl)-3-(3-dimethylaminopropyl)-4,4-dimethylpiperidine-2,6-dione (AGN 2979) bisulphate.

The bisulphate salts of the invention can be prepared by conventional techniques for converting a free base into an acid addition salt or for converting one acid addition salt to another. In a presently preferred process, the bisulphate salt is prepared by treating an ethanol solution of a compound of Formula 1 with a cooled solution of sulphuric acid in ethanol; evaporation of the solvent under reduced pressure and recrystallisation of the residue from ethanol.

The compounds of Formula 1 can be prepared by the processes disclosed in U.S. Pat. No. 3,963,729 or U.S. Pat. No. 5,104,990, the disclosure of which documents are incorporated by this reference. The optical isomers can be separated in conventional manner, for example the (−) isomers can be separated by crystallisation of their (+) binaphthyl phosphoric acid salts from a suitable solvent such as ethanol.

The bisulphate salts of the compounds of Formula 1 have the same pharmacological activity as that previously reported for the free base and other acid addition salts, especially the hydrochloride, and is especially useful for the treatment or prophylaxis of any stress-induced affective disorder. As mentioned above, the term "stress-induced affective disorder" is used herein to include any disorder associated with elevated levels of 5-HT (5-hydroxytryptamine; serotonin) resultant from newly synthesised 5-HT. In particular, the bisulphate salts can be used to treat or prevent those neurological and psychological diseases and conditions in which newly synthesised 5-HT is implicated and for which antidepressant, anxiolytic and antipsychotic drugs are presently indicated. Non-limiting examples of such diseases or conditions are agoraphobia; anorexia nervosa; anxiety; anxiogenisis associated with withdrawal from drugs of abuse; bulimia nervosa; chronic paroxysmal hemicrania; depression (including prevention of depressive recurrences); diminution of the immune response associated with anxiety, depression or bereavement; disorders of sleep initiation or maintenance; disorders of the sleep-awake schedule; dream anxiety attacks; Huntington's chorea; Kleine-Levin syndrome; memory disturbance; Ménière's disease, menstrual-associated sleep syndrome; migraine; motion sickness; nausea incompletely relieved by $5HT_3$ antagonist administration, neurogenic pain; neuropathic pain; obsessive-compulsive disorder; panic attacks; post-traumatic stress disorder; pre-menstrual dysphoric disorder; recurrent brief depression; Restless Leg syndrome, schizophrenia; senile dementia; serotonin-irritation syndrome; sleep apnoea; sleep related cardiovascular symptoms; sleep related epileptic seizures; sleep-related cluster headaches; sleep-related myoclomus syndrome; social phobia; sudden infant death syndrome; and tinnitus.

The bisulphate salts of the invention can be administered in any of the manners previously proposed for the hydrochloride salt. They can be administered alone or in the form of pharmaceutical preparations to the patient being treated either orally or parenterally, for example subcutaneously or intravenously. The amount of bisulphate salt administered will vary and can be any effective amount. Depending upon the patient and the mode of administration, the quantity of bisulphate salt administered may vary over a wide range to provide from about 0.1 mg/kg to about 20 mg/kg, usually about 0.5 mg/kg to about 10 mg/kg and preferably about 1 to about 5 mg/kg, of body weight of the patient per dose. Unit doses of these salts can contain, for example, from about 10 mg to about 500 mg, advantageously about 25 to about 200 mg. usually about 50 to about 100 mg of the bisulphate salt and may be administered, for example, from 1 to 4 times daily. The term "unit dosage form" is used herein to mean a single or multiple dose form containing a quantity of the active ingredient in admixture with or otherwise in association with a diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

The pharmaceutical formulations in which form the bisulphate salts of the invention will normally be utilised are prepared in a manner well known per se in the pharmaceutical art and usually comprise at least one active bisulphate salt of the invention in admixture or otherwise in association with a pharmaceutically acceptable carrier or diluent therefor. For making those formulations, the active ingredient usually will be mixed with a carrier, or diluted by a diluent, or enclosed or encapsulated in a capsule, sachet, cachet, paper or other container. A carrier or diluent may be solid, semi-solid or liquid material that serves as a vehicle, excipient or medium for the active ingredient. Suitable carriers or diluents are well known per se. The formulations may be adapted for enteral or parenteral use and may be administered to the patient in the form of tablets, capsules, dragees, suppositories, syrups, suspensions or the like.

Figure 1:
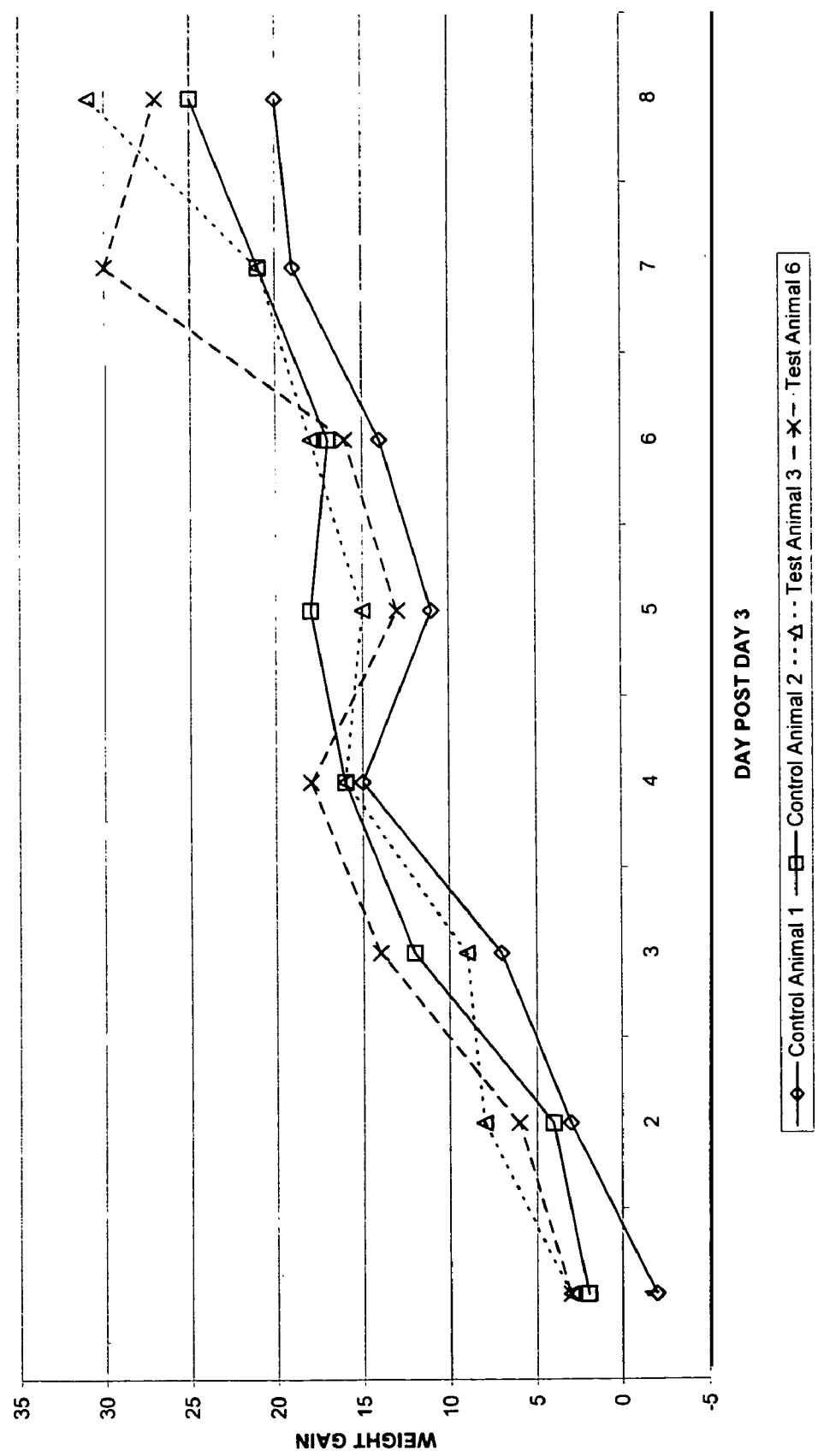
FIG. 1 is a graph of "WEIGHT GAIN" versus "DAY POST DAY 3" and shows results for Example 8 for rats 3 and 6.

The invention is illustrated in the following non-limiting Examples.

EXAMPLE 1

Preparation of 3(3-methoxyphenyl)-3-(3-dimethylaminopropyl)-4,4-dimethyl-piperidine-2,6-dione bisulphate (AGN 2979 bisulphate)

A cooled solution of sulphuric acid (9.8 g) in ethanol (100 cm$^3$) was mixed into an ethanol solution of 3(3-methoxyphenyl)-3-(3-dimethylaminopropyl)-4,4-dimethylpiperidine-2,6-dione (AGN 2979) (33.25 g). Substantially immediately after mixing, the solvent was evaporated under reduced pressure and the residue recrystallised from ethanol to yield AGN 2979 bisulphate as crystals having a melting point of 164° C. After storage for a prolonged period in a non-air tight container, a sample had a portion which melted at 110° C. but the bulk of the sample melted at 164° C., indicating the presence of a hydrate.

EXAMPLE 2

Preparation of 3(3-methoxyphenyl)-3-(3-dimethylaminopropyl)-4,4-dimethyl-piperidine-2,6-dione bisulphate (AGN 2979 bisulphate)

(A) Preparation of diethyl 2-[2-cyano-5-(dimethylamino)-2-(3-methoxy-phenyl)-1,1-dimethylpentyl]propanedioate, monohydrochloride

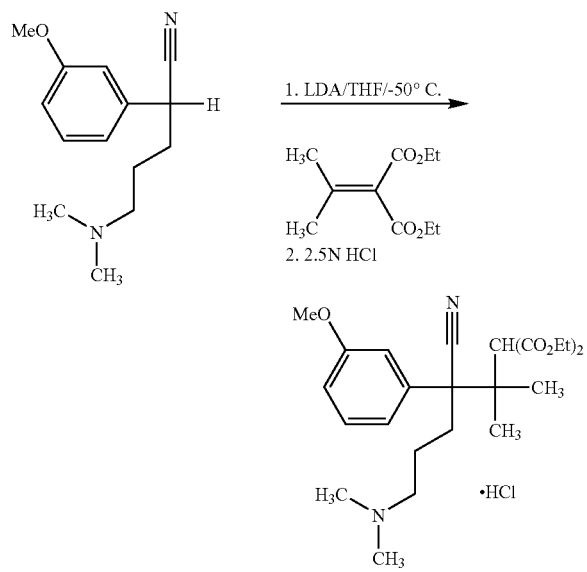

A nitrogen atmosphere was applied to a reaction vessel and 50 ml of dry tetrahydrofuran is added. The solvent was cooled to less than −40° C. and 32 mmoles of lithium diisopropylamide in tetrahydrofuranne-heptane was added (16 ml of a 2 M solution). A solution of 6.97 g (30 mmoles) of α-[3-(dimethylamino)propyl]-3-methoxybenzeneacetonitrile in 30 ml of tetrahydrofuran was added at less than −20° C. and left at this temperature for 30 min. The mixture was then cooled to −50° C. and a solution of 6.62 g (33 mmoles) of diethyl isopropylidenemalonate in 30 ml of tetrahydrofuran was added to the reaction mixture at a rate such that the temperature did not exceed −50° C. The mixture was stirred at −50° C. for 30 min and the cold reaction mixture added to a stirred solution of 30 ml of aqueous hydrochloric acid (36% w/w) in 100 ml of water cooled to 10° C. The mixture was extracted twice with toluene and the toluene phase is back extracted with a solution of 2 ml of hydrochloric acid (36% w/w) in 8 ml of water. The aqueous acidic extract was combined with the aqueous acidic phase from above and extracted twice with 50 ml portions of methylene chloride. The combined methylene chloride extracts were washed with water and the methylene chloride phase filtered and concentrated to low volume by distillation at atmospheric pressure. A 100 ml portion of ethyl acetate was added and the resulting slurry cooled to 5–10° C. The resulting solid was collected by filtration, washed with ethyl acetate and dried at 50° C. to give 10.1 g of white powder.

(B) Preparation of 3-(3-methoxyphenyl)-3-(3-dimethylaminopropyl]-4,4-dimethyl-piperidine-2,6-dione bisulphate salt (anhydrous)

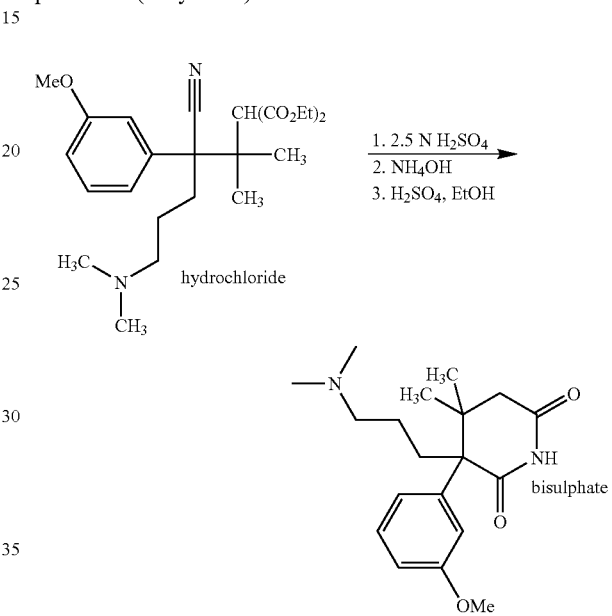

A 250 ml round-bottomed flask was charged with 10 g of the above-prepared diethyl 2-[2-cyano-5-(dimethylamino)-2-(3-methoxyphenyl)-1,1-dimethylpentyl]-propanedioate mono-hydrochloride, and a solution of 10.2 g of sulphuric acid (96% w/w) in 90 ml of water was added. The reaction mixture was refluxed for about 54 hours. When the reaction was complete (as indicated by thin layer chromatography) the solution was cooled to 25° C. The aqueous solution was washed with methylene chloride, the aqueous phase mixed with methylene chloride and basified with aqueous ammonium hydroxide (29% w/w) while maintaining the temperature at less than 30° C. After separation of the layers, the aqueous phase was extracted twice with methylene chloride, the combined organic phases concentrated and the residue crystallised in tert-butyl methyl ether to give 5.7 g of white powder. The crude compound was suspended in 200 ml of absolute ethyl alcohol, 1 equivalent of concentrated sulphuric acid added and the mixture is heated under reflux for 30 minutes to dissolve the salt. After cooling, most of the solvent was evaporated under reduced pressure and the residue was by crystallised means of a 50/50 mixture of diethylether-ethyl alcohol to give 6 g of white powder (melting point=159°–161° C.) and dried under reduced pressure.

(C) Preparation of 3-(3-methoxyphenyl)-3-(3-dimethylaminopropyl]-4,4-dimethyl-piperidine-2,6-dione bisulphate salt (sesquihydrate)

50 μl of water (1.6 mmoles) were added to a suspension of the above anhydrous bisulphate (430 mg, 1 mmole) in 25 ml of isopropanol and the slurry heated to complete dissolution of the salt. After slow cooling, the sesquihydrate salt crystallised and was filtered off and the crystals dried at room temperature. Their melting point is 150°–152° C.

EXAMPLE 3

Tablets each having the following composition are prepared by conventional tabletting techniques:

| Ingredient | mg per tablet |
| --- | --- |
| (a) AGN 2979 bisulphate | 50 |
| (b) Lactose | 51.5 |
| (c) Maize starch dried | 45 |
| (d) magnesium stearate | 1.5 |

EXAMPLE 4

Suppositories are formed from the following composition:

| Ingredient | mg/suppository |
| --- | --- |
| (a) AGN 2979 bisulphate | 20 |
| (b) Oil of Theobroma (cocoa butter) | 980 |

The compound (a) is powdered and passed through a BS No. 100 sieve (0.125 mm) and triturated with molten oil of Theobroma at 45° C. to form a smooth suspension. The mixture is well stirred and poured into moulds each of nominal 1 g capacity to produce suppositories.

EXAMPLE 5

Pills each having the following composition are prepared by blending the active (a) and the corn starch (b), then adding the liquid glucose (c) with thorough kneading to form a plastic mass from which the pills are cut and formed:

| Ingredient | per pill |
| --- | --- |
| (a) AGN 2979 bisulphate | 50 mg |
| (b) Corn starch | 45 mg |
| (c) Liquid glucose | 7 cm$^3$ |

EXAMPLE 6

Gelatine capsules each containing 50 mg AGN 2979 bisulphate and 20 mg talc are prepared by passing AGN 2979 and talc separately through a fine mesh screen, mixing the sieved powders and filling the mixed powder into hard gelatine capsules at a net fill of 70 mg per capsule.

EXAMPLE 7

Antidepressant Activity of AGN 2979 bisulphate

Male Wistar rats were brought into the laboratory 2 months before the start of the experiment, at which time they weighed approx. 300 g. Except as described below, all animals were singly housed, with food and water freely available, and maintained on a 12-hour light/dark. The animals were first trained to consume a 1% sucrose solution. Training consisted of nine 1-hour baseline tests in which sucrose was presented in pre-weighed bottles, in the home cage, and, following 14 hours food and water deprivation; the sucrose intake was measured by weighing the pre-weighed bottles at the end of the test. Subsequently, sucrose consumption was monitored, under similar conditions, at weekly intervals throughout the whole experiment.

On the basis of their sucrose intakes in the final baseline test, the animals were divided into two matched groups. One group of animals was subjected to a chronic mild stress ("CMS") procedure for a period of 9 consecutive weeks. Each week of stress regime consisted of: two periods of food or water deprivation, two periods of 45 degree cage tilt, two periods of intermittent illumination (lights on and off every 2 hours), two periods of soiled cage (250 ml water in sawdust bedding), two periods of paired housing, two periods of low intensity stroboscopic illumination, and two periods of no stress. All stressors were of 10–14 hours duration and were applied individually and continuously, day and night. Control animals were housed in a separate room and had no contact with the stressed animals. They were deprived of food and water for the 14 hours preceding each sucrose test, but otherwise food and water were freely available in the home cage. On the basis of their sucrose intake scores following an initial 3 weeks of stress, both stressed and control animals were each divided further into matched subgroups (n=8), and, for the subsequent 5 weeks, they received daily administrations of vehicle (1 cm$^3$/kg, p.o.), AGN 2979 bisulphate (1, 4 and 16 mg/kg, p.o.) or imipramine (10 mg/kg, i.p. (i.e. by intraperitoneal injection). At a dose of 10 mg/kg, i.p, imipramine causes stabile and comparable effects in the CMS model, and therefore, has been used as the reference treatment in most CMS comparative studies. The drugs were administered at approximately 10.00 am, and sucrose tests were carried out 24 hours following the last drug treatment. After five weeks, all treatments were terminated and after one week of withdrawal a final sucrose test was carried out. Stress was continued throughout the period of treatment and withdrawal.

Chronic mild stress causes a gradual decrease in the consumption of 1% sucrose solution. In the final baseline test, all animals drank approximately 12 g of sucrose solution. Following initial three weeks of stress, intakes remained at the same level in control animals but fell to 7.5 (±0.3) g in stressed animals. Such a difference between control and stressed animals treated with vehicle, persisted at similar level for the remainder of the experiment [Group effect: $F(1,98)=67.256$; $P<0.001$].

In control animals, the consumption of sucrose solution was not changed by imipramine [$F(1,84)=0.919$; NS] and any of three doses of AGN 2979 bisulphate [$F(3, 168)=1, 698$; NS], but in stressed animals both agents caused a gradual increase of sucrose intake, resulting in a significant treatment effect [imipramine: $F(1,84)=21.467$; $p<0.001$, AGN 2979: $F(3, 168)=8.315$; $p<0.001$]. The sucrose intake in imipramine-treated stressed animals was significantly increased from initial scores (Week 0) after three weeks of treatment (p=0.01) and after five weeks of treatment there were no significant differences between drug-treated stressed and vehicle-treated control animals (p=0.851).

Only the dose of 4 mg/kg of AGN 2979 bisulphate was active [$F(1,84)=24.574$; $p<0.001$] and caused significant increase of sucrose intake already within the first week of treatment (p=0.008). This effect was maintained at a similar level thereafter, and at the end of treatment period (Week 5) the amount of sucrose solution drunk by stressed animals receiving this dose of AGN 2979 bisulphate was comparable to that of vehicle-treated controls (p=0.536) and significantly higher than that of vehicle-treated stressed animals (p=0.048). At the two other doses tested in this study, AGN 2979 bisulphate was ineffective against the stress-induced deficit in the consumption of sucrose solution and the stressed animals treated with these doses did not significantly differ from the vehicle-treated stressed animals throughout the whole period of treatment [1 mg/kg: $F(1,84)=0.008$; NS, 16 mg/kg: $F(1,84)=0.207$; NS]. Both control and stressed animals receiving the highest dose of AGN 2979 bisulphate (16 mg/kg) showed some behavioural impairments They included sedation, hypoactivity (but not catalepsy) and hyporeactivity to handling and drug injections. These effects commenced at the beginning of the drug administration but disappeared at the end of third week of treatment.

One week after withdrawal from the treatment with imipramine and AGN 2979 bisulphate, the consumption of sucrose solution was comparable to that observed in Week 5 of treatment, and the overall effect of withdrawal in all drug-treated groups was not significant in both control $[F(6,98)=1.410$; NS] and stressed animals $[F(6,98)=1.507$; NS].

The CMS decreased the body weights of animals receiving vehicle for five weeks but this effect did not reach statistical significance $[F(3, 14)=2.092$; NS]. Chronic treatment with vehicle, imipramine and AGN 2979 bisulphate had no significant effect on body weights of control $[F(3, 28)=1.035$; NS] and stressed animals $[F(3,28)=2.484$; NS].

The study demonstrates that chronic administration of AGN 2979 bisulphate can normalize the behavioural deficit produced in an animal model of depression and confirms the previous clinical reports demonstrating that AGN 2979 hydrochloride is effective in alleviating depression. The activity of AGN 2979 bisulphate in the CMS model has several parallels with that of imipramine. In particular, the increases in sucrose intakes were observed only in animals subjected to the CMS procedure and both drugs normalized the CMS-induced behavioural deficit without any significant effect on body weight (as found in similar tests using AGN 2979 hydrochloride). This confirms previous reports that the therapeutic activity of drugs in the CMS model cannot be attributed to changes in the weight of animals. Also the magnitude of the effect of AGN 2979 bisulphate in the CMS model was comparable to that of imipramine; at the end of the treatment period a full recovery from the CMS-induced behavioural deficit was observed. This effect was maintained for at least one week after cessation of treatment, and no signs of withdrawal were observed in either stressed or control animals receiving AGN 2979 bisulphate or imipramine. This is consistent with previous clinical observations that AGN 2979 hydrochloride does not cause any adverse effects following discontinuation of chronic administration of the compound.

Although AGN 2979 bisulphate and imipramine were equally effective in completely reversing the effect of stress, AGN 2979 bisulphate had a more rapid onset of action, with significant effects observed within the first week of treatment, compared with a lag phase of three weeks for imipramine. This finding confirms results obtained in an earlier clinical trial with AGN 2979 hydrochloride that the onset of antidepressant action of AGN 2979 may be faster than that of other antidepressants. The comparison of the speed of action of AGN 2979 bisulphate and imipramine is limited by the fact that, in this study, imipramine was tested at a single dose of 10 mg/kg. However, in earlier studies imipramine was administered at a dose of 20 mg/kg per day and caused similar effects, both in terms of the magnitude and the time-course. Also other drugs such as amitriptyline, buspirone, and citalopram were not more effective against the CMS-induced anhedonia when their doses were increased above the threshold active ones. In all studies with the CMS model various classes of antidepressant drugs (i.e. tricyclics, "atypical" agents, selective serotonin reuptake inhibitors, and monoamine oxidase inhibitors), required at least three to five weeks of treatment before they could reverse the stress-induced behavioural deficit, and the only treatment which has been shown to restore normal responsiveness to reward in stressed animals after a single week of administration was electroconvulsive shock.

The antidepressant-like effect of AGN 2979 bisulphate in the CMS model was not dose-dependent; only the intermediate dose of 4 mg/kg, corresponding to the clinically effective dose of 200–400 mg/day, being active. At the higher dose of 16 mg/kg, AGN 2979 bisulphate was ineffective against the CMS-induced deficit in sucrose consumption. There is no obvious explanation for this observation but it can be speculated that the loss of activity at the higher dose of AGN 2979 bisulphate in the CMS model could result from other than antidepressant-related effects as both the stressed and control animals receiving this dose showed signs of sedation, hypoactivity and hyporeactivity. Similar behavioural impairments caused by inhibition of tryptophan hydroxylase have been also observed in other studies.

The antidepressant action of AGN 2979 bisulphate appears to result from the inhibition of tryptophan hydroxylase activation, and the mechanism of this effect may involve blockade of K+ channels since other metabolic inhibitors, such as guanidine and sodium cyanide, which are known to open K+ channels, can activate tryptophan hydroxylase and this activation can be blocked by AGN 2979 bisulphate.

EXAMPLE 8

Effect of AGN 2979 bisulphate on Rat Weight

Figure 2:
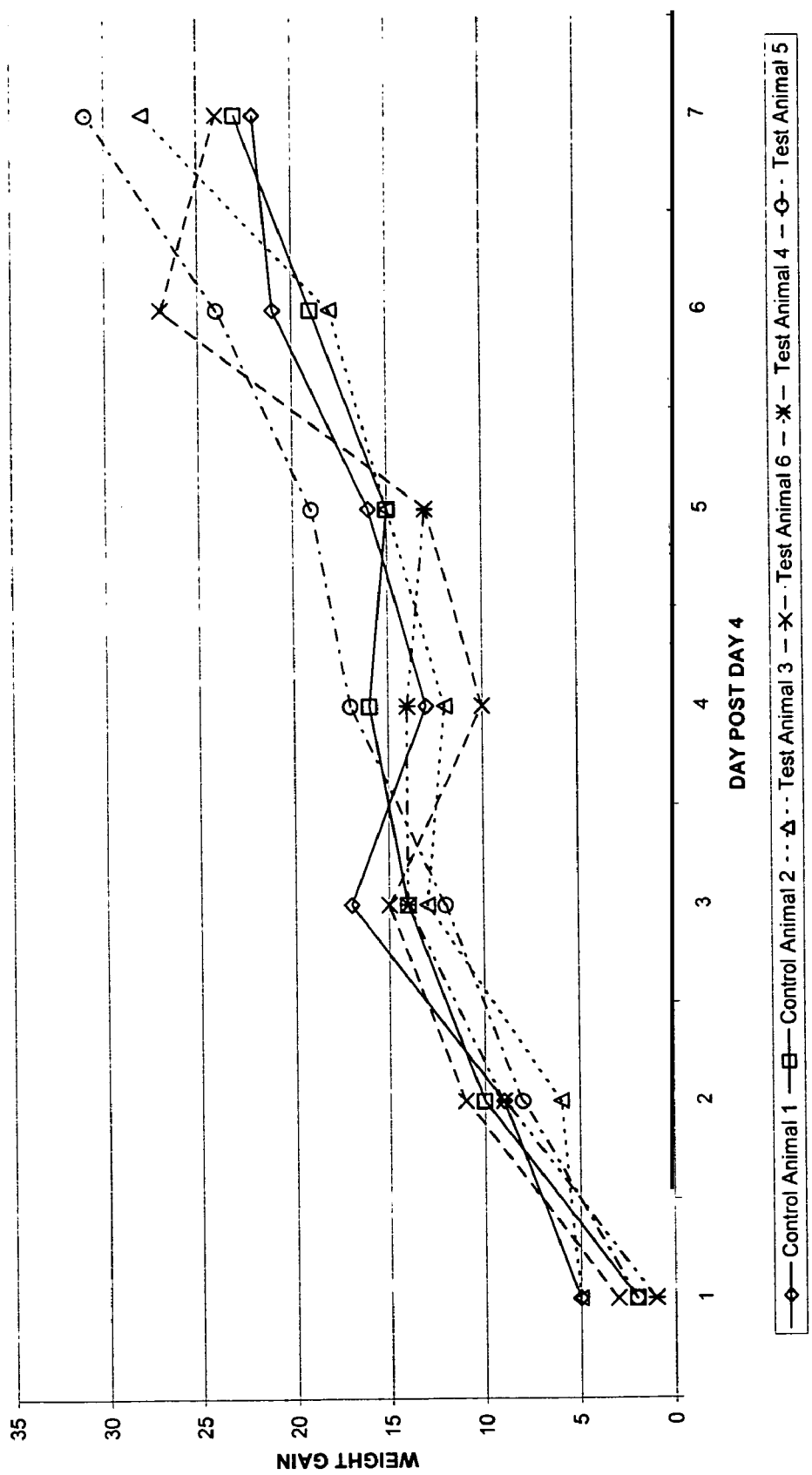
FIG. 2 is a graph of "WEIGHT GAIN" versus "DAY POST DAY 4" and shows results for Example 8 for all rats.

4 Male Spraque-Dawley rats were fed with their standard laboratory diet to which had been added 0.36% AGN 2979 bisulphate for a period of 9 days and their weight monitored on a daily basis and compared with 2 control rats receiving the standard laboratory diet without the bisulphate. For a rat weighing 360 g and consuming 23 g of the diet, the amount of AGN 2979 bisulphate consumed was about 230 mg/kg. The results are shown in Table 1 below, in which the bisulphate is identified as "AGN 2979 BS". It will be noted that after an initial period of 3 or 4 days during which the test rats were becoming accustomed to the new diet, the weight gain of the test rats was the same as that of the control rats. In contrast, it is known from previous experiments that the corresponding dose (200 mg/kg) of AGN 2979 hydrochloride produces a continuing weight disparity (loss) in test rats compared with control rats. In particular, the test rats lost or merely maintained their body weight. The weight gains after an initial 3 day period for the two control rats and for test rats 3 and 6 are shown graphically in FIG. 1 and the weight gains for all 6 rats after an initial 4 day period are shown in FIG. 2.

TABLE 1

| | | | Food | | | Animal Weight | | | Total Gain | Total Gain |
|---|---|---|---|---|---|---|---|---|---|---|
| Day | Animal | Treatment | Start (g) | Finish (g) | Eaten (g) | Start (g) | Finish (g) | Daily Gain (g) | (after day 3) (g) | (after day 4) (g) |
| 1 | 1 | none | 89.1 | 63.1 | 26 | 362 | 368 | +6 | — | — |
| | 2 | none | 92.6 | 67.4 | 25.2 | 396 | 404 | +8 | — | — |
| | 3 | AGN 2979 BS | 85.4 | 70.6 | 14.8 | 364 | 369 | +5 | — | — |
| | 4 | AGN 2979 BS | 93.4 | 77.5 | 15.9 | 375 | 370 | −5 | — | — |
| | 5 | AGN 2979 BS | 95.6 | 75.5 | 20.1 | 364 | 371 | +7 | — | — |
| | 6 | AGN 2979 BS | 99 | 73 | 26 | 367 | 378 | +11 | — | — |
| 2 | 1 | none | 95.6 | 73.3 | 22.3 | 368 | 371 | +3 | — | — |
| | 2 | none | 96.6 | 71 | 25.6 | 404 | 406 | +2 | — | — |
| | 3 | AGN 2979 BS | 90.8 | 71.9 | 18.9 | 369 | 360 | −9 | — | — |
| | 4 | AGN 2979 BS | 99.5 | 83.1 | 16.4 | 370 | 367 | −3 | — | — |
| | 5 | AGN 2979 BS | 99.1 | 87.8 | 11.3 | 371 | 360 | −11 | — | — |
| | 6 | AGN 2979 BS | 97.7 | 75.9 | 21.8 | 378 | 374 | −4 | — | — |
| 3 | 1 | none | 89.4 | 62.8 | 26.6 | 371 | 377 | +6 | — | — |
| | 2 | none | 89.3 | 64.5 | 24.8 | 406 | 407 | +1 | — | — |
| | 3 | AGN 2979 BS | 85.3 | 67.8 | 17.5 | 360 | 358 | −2 | — | — |
| | 4 | AGN 2979 BS | 96.3 | 75.8 | 20.5 | 367 | 368 | +1 | — | — |
| | 5 | AGN 2979 BS | 100.2 | 81.8 | 18.4 | 360 | 361 | +1 | — | — |
| | 6 | AGN 2979 BS | 97.8 | 76.9 | 20.9 | 374 | 371 | −3 | — | — |
| 4 | 1 | none | 89.5 | 62.9 | 26.6 | 377 | 375 | −2 | −2 | — |
| | 2 | none | 90.7 | 64.8 | 25.9 | 407 | 409 | +2 | +2 | — |
| | 3 | AGN 2979 BS | 86.9 | 63.8 | 23.1 | 358 | 361 | +3 | +3 | — |
| | 4 | AGN 2979 BS | 99.5 | 84 | 15.5 | 368 | 361 | −7 | — | — |
| | 5 | AGN 2979 BS | 96 | 78.8 | 17.2 | 361 | 357 | −4 | — | — |
| | 6 | AGN 2979 BS | 96.8 | 74.4 | 22.4 | 371 | 374 | +3 | +3 | — |
| 5 | 1 | none | 91.3 | 65.8 | 25.5 | 375 | 380 | +5 | +3 | +5 |
| | 2 | none | 93.9 | 66.2 | 27.7 | 409 | 411 | +2 | +4 | +2 |
| | 3 | AGN 2979 BS | 81.3 | 57.6 | 23.7 | 361 | 366 | +5 | +8 | +5 |
| | 4 | AGN 2979 BS | 97.8 | 78.4 | 19.4 | 361 | 362 | +1 | — | +1 |
| | 5 | AGN 2979 BS | 98.5 | 78.1 | 20.4 | 357 | 359 | +2 | — | +2 |
| | 6 | AGN 2979 BS | 97.5 | 72.4 | 25.1 | 374 | 377 | +3 | +6 | +3 |
| 6 | 1 | none | 94.3 | 68.3 | 26 | 380 | 384 | +4 | +7 | +9 |
| | 2 | none | 96.1 | 66.8 | 29.3 | 411 | 419 | +8 | +12 | +10 |
| | 3 | AGN 2979 BS | 85.1 | 60.4 | 24.7 | 366 | 367 | +1 | +9 | +6 |
| | 4 | AGN 2979 BS | 102.3 | 77.3 | 25 | 362 | 370 | +8 | — | +9 |
| | 5 | AGN 2979 BS | 92.7 | 71.2 | 21.5 | 359 | 365 | +6 | — | +8 |
| | 6 | AGN 2979 BS | 94.1 | 68.3 | 25.8 | 377 | 385 | +8 | +14 | +11 |
| 7 | 1 | none | 89.5 | 63.9 | 25.6 | 384 | 392 | +8 | +15 | +17 |
| | 2 | none | 93.8 | 70.6 | 23.2 | 419 | 423 | +4 | +16 | +14 |
| | 3 | AGN 2979 BS | 83 | 59.1 | 23.9 | 367 | 374 | +7 | +16 | +13 |
| | 4 | AGN 2979 BS | 101.9 | 79.7 | 22.2 | 370 | 375 | +5 | — | +14 |
| | 5 | AGN 2979 BS | 93.8 | 76.1 | 17.7 | 365 | 369 | +4 | — | +12 |
| | 6 | AGN 2979 BS | 94.5 | 72.6 | 21.9 | 385 | 389 | +4 | +18 | +15 |
| 8 | 1 | none | 97.1 | 71.9 | 25.2 | 392 | 388 | −4 | +11 | +13 |
| | 2 | none | 97.7 | 68.6 | 29.1 | 423 | 425 | +2 | +18 | +16 |
| | 3 | AGN 2979 BS | 86.3 | 61.6 | 24.7 | 374 | 373 | −1 | +15 | +12 |
| | 4 | AGN 2979 BS | 94.6 | 72.3 | 22.3 | 375 | 375 | 0 | — | +14 |
| | 5 | AGN 2979 BS | 91.4 | 69.4 | 22 | 369 | 374 | +5 | — | +17 |
| | 6 | AGN 2979 BS | 95.2 | 74.8 | 20.4 | 389 | 384 | −5 | +13 | +10 |
| 9 | 1 | none | 93.3 | 68.6 | 24.7 | 388 | 391 | +3 | +14 | +16 |
| | 2 | none | 92.4 | 67.4 | 25 | 425 | 424 | −1 | +17 | +15 |
| | 3 | AGN 2979 BS | 81.8 | 55.8 | 26 | 373 | 376 | +3 | +18 | +15 |
| | 4 | AGN 2979 BS | 91.4 | 71.2 | 20.2 | 375 | 374 | −1 | — | +13 |
| | 5 | AGN 2979 BS | 88.7 | 66.6 | 22.1 | 374 | 376 | +2 | — | +19 |
| | 6 | AGN 2979 BS | 99.6 | 76.9 | 22.7 | 384 | 387 | +3 | +16 | +13 |
| 10 | 1 | none | 92 | 64.3 | 27.7 | 391 | 396 | +5 | +19 | +21 |
| | 2 | none | 93.8 | 64.2 | 29.6 | 424 | 428 | +4 | +21 | +19 |
| | 3 | none | 81.5 | 55.5 | 26 | 376 | 379 | +3 | +21 | +18 |
| | 4 | — | — | — | — | — | — | — | — | — |
| | 5 | none | 90.2 | 64.8 | 25.4 | 376 | 381 | +5 | — | +24 |
| | 6 | none | 98.6 | 71.5 | 27.1 | 387 | 401 | +14 | +30 | +27 |
| 11 | 1 | none | 94.6 | 74 | 20.6 | 396 | 397 | +1 | +20 | +22 |
| | 2 | none | 95 | 73 | 22 | 428 | 432 | +4 | +25 | +23 |
| | 3 | none | 80.3 | 51.4 | 28.9 | 379 | 389 | +10 | +31 | +28 |
| | 4 | — | — | — | — | — | — | — | — | — |
| | 5 | none | 95.4 | 72.5 | 22.9 | 381 | 388 | +7 | — | +31 |
| | 6 | none | 85.4 | 63.6 | 21.8 | 401 | 398 | −3 | +27 | +24 |

EXAMPLE 9

A male subject aged 67 years, height 178 cm and weighing 90 kilograms having had persistent awakening episodes of obstructive sleep apnoea (manifested by nocturnal choking) had been treated for several years with AGN 2979 hydrochloride, initially at a daily oral dose level of 120 mg and subsequently at a single oral maintenance dose of 120 mg every 4 days. The hydrochloride salt was replaced with the bisulphate salt at a single oral maintenance dose of 65 mg every two days with continued absence of awakening episodes and no side effects. When administration of the AGN 2979 sulphate recently was suspended, nocturnal choking returned after three weeks. The patient also reports that previous regular bouts of seasickness have been not recurred since treatment with AGN 2979 bisulphate.

The invention claimed is:

1. A bisulphate salt of a 3-phenyl-3-dimethylaminoalkyl-4,4-dimethylpiperidin-2,6-dione of Formula I:

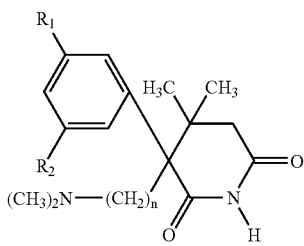

(I)

wherein:

$R_1$ represents methoxy, ethoxy or hydroxy;

$R_2$ represents methoxy, ethoxy, hydroxy or hydrogen; and n represents 2 or 3, or a pharmacologically acceptable hydrate thereof.

2. A bisulphate salt as claimed in claim 1, wherein $R_1$ represents methoxy and $R_2$ represents methoxy or hydrogen.

3. A bisulphate salt as claimed in claim 2, wherein the bisulphate salt is 3(3-methoxyphenyl)-3-(3-dimethylaminopropyl)-4,4-dimethylpiperidine-2,6-dione bisulphate.

4. A bisulphate salt as claimed in claim 2, wherein the bisulphate salt is 3(3,5-dimethoxyphenyl)-3-(3-dimethylaminopropyl)-4,4-dimethylpiperidine-2,6-dione bisulphate.

5. A bisulphate salt as claimed in claim 1, wherein the bisulphate salt is in the form of its (−) isomer.

6. A bisulphate salt as claimed in claim 1, wherein the bisulphate salt is anhydrous.

7. A bisulphate salt as claimed in claim 1, wherein the bisulphate salt in the form of the sesquihydrate.

8. A pharmaceutical composition comprising a bisulphate salt of a 3-phenyl-3-dimethylaminoalkyl-4,4-dimethylpiperidin-2,6-dione of Formula I:

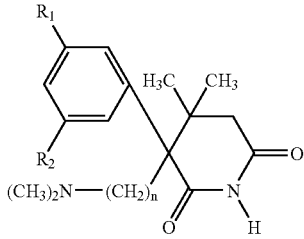

(I)

wherein:

$R_1$ represents methoxy, ethoxy or hydroxy;

$R_2$ represents methoxy, ethoxy, hydroxy or hydrogen; and n represents 2 or 3, or a pharmacologically acceptable hydrate thereof and a pharmacologically acceptable diluent or carrier.

9. A pharmaceutical composition as claimed in claim 8 for the treatment or prophylaxis of a stress-related affective disorder.

10. A pharmaceutical composition as claimed in claim 8, wherein $R_1$ represents methoxy and $R_2$ represents methoxy or hydrogen.

11. A pharmaceutical composition as claimed in claim 10, wherein the bisulphate salt is 3(3-methoxyphenyl)-3-(3-dimethylaminopropyl)-4,4-dimethylpiperidine-2,6-dione bisulphate.

12. A pharmaceutical composition as claimed in claim 10, wherein the bisulphate salt is 3(3,5-dimethoxyphenyl)-3-(3-dimethylaminopropyl)-4,4-dimethylpiperidine-2,6-dione bisulphate.

13. A method for the treatment of depression in a human or animal patient in need of such treatment, which comprises administering to the human or animal patient a therapeutically effective amount of a compound of claim 1.

14. A method for the treatment of anxiety in a human or animal patient in need of such treatment, which comprises administering to the human or animal patient a therapeutically effective amount of a compound of claim 1.

15. A method for the treatment of sleep apnea in a human or animal patient in need of such treatment, which comprises administering to the human or animal patient a therapeutically effective amount of a compound of claim 1.

16. A method as claimed in claim 13, wherein the bisuphate salt is 3(3-methoxyphenyl)-3-(3-dimethylaminopropyl)-4,4-dimethylpiperidine-2,6-dione bisulphate.

17. A method as claimed in claim 14, wherein the bisuphate salt is 3(3-methoxyphenyl)-3-(3-dimethylaminopropyl)-4,4-dimethylpiperidine-2,6-dione bisulphate.

18. A method as claimed in claim 15, wherein the bisuphate salt is 3(3-methoxyphenyl)-3-(3-dimethylaminopropyl)-4,4-dimethylpiperidine-2,6-dione bisulphate.

19. A method as claimed in claim 13, wherein the bisulphate salt is 3(3,5-dimethoxyphenyl)-3-(3-dimethylaminopropyl)-4,4-dimethylpiperidine-2,6-dione bisulphate.

20. A method as claimed in claim 14, wherein the bisulphate salt is 3(3,5-dimethoxyphenyl)-3-(3-dimethylaminopropyl)-4,4-dimethylpiperidine-2,6-dione bisulphate.

21. A method as claimed in claim 15, wherein the bisulphate salt is 3(3,5-dimethoxyphenyl)-3-(3-dimethylaminopropyl)-4,4-dimethylpiperidine-2,6-dione bisulphate.

* * * * *